(12) United States Patent
Rentea et al.

(10) Patent No.: US 7,613,510 B2
(45) Date of Patent: Nov. 3, 2009

(54) BIOFEEDBACK DEVICE DISPLAYING RESULTS ON A CELLULAR PHONE DISPLAY

(76) Inventors: Razvan Rentea, 3525 W. Peterson, Suite 611, Chicago, IL (US) 60659;
Christopher J. P. Dawes, 3525 W. Peterson, Suite 611, Lake Forest, IL (US) 60659

(*) Notice: Subject to any disclaimer, the term of this patent is extended or adjusted under 35 U.S.C. 154(b) by 0 days.

(21) Appl. No.: 10/734,066

(22) Filed: Dec. 11, 2003

(65) Prior Publication Data
US 2004/0204633 A1  Oct. 14, 2004

Related U.S. Application Data

(60) Provisional application No. 60/432,767, filed on Dec. 12, 2002.

(51) Int. Cl.
*A61H 39/02* (2006.01)
(52) U.S. Cl. .................... 600/548; 600/546
(58) Field of Classification Search ......... 600/300–301, 600/547, 548; 128/903–905, 920–921; 434/236–238, 434/262
See application file for complete search history.

(56) References Cited

U.S. PATENT DOCUMENTS

| | | | |
|---|---|---|---|
| 5,755,577 A | 5/1998 | Gillio | |
| 6,259,889 B1 | 7/2001 | LaDue | |
| 6,309,342 B1 | 10/2001 | Blazey et al. | |
| 6,327,495 B1 * | 12/2001 | Iwabuchi et al. | 600/547 |
| 6,330,885 B1 | 12/2001 | Weissman et al. | |
| 6,386,882 B1 | 5/2002 | Linberg | |
| 6,421,560 B1 | 7/2002 | Yoo | |
| 6,468,222 B1 | 10/2002 | Mault et al. | |
| 6,478,736 B1 * | 11/2002 | Mault | 600/300 |
| 6,865,410 B2 * | 3/2005 | Kavet et al. | 600/547 |

* cited by examiner

*Primary Examiner*—Max Hindenburg
*Assistant Examiner*—Jonathan M Foreman
(74) *Attorney, Agent, or Firm*—Brinks Hofer Gilson & Lione

(57) ABSTRACT

Biofeedback information is measured at a body part of a user. The information is communicated to a cellular telephone device and used to produce a display on a display screen of the cellular telephone device.

4 Claims, 9 Drawing Sheets

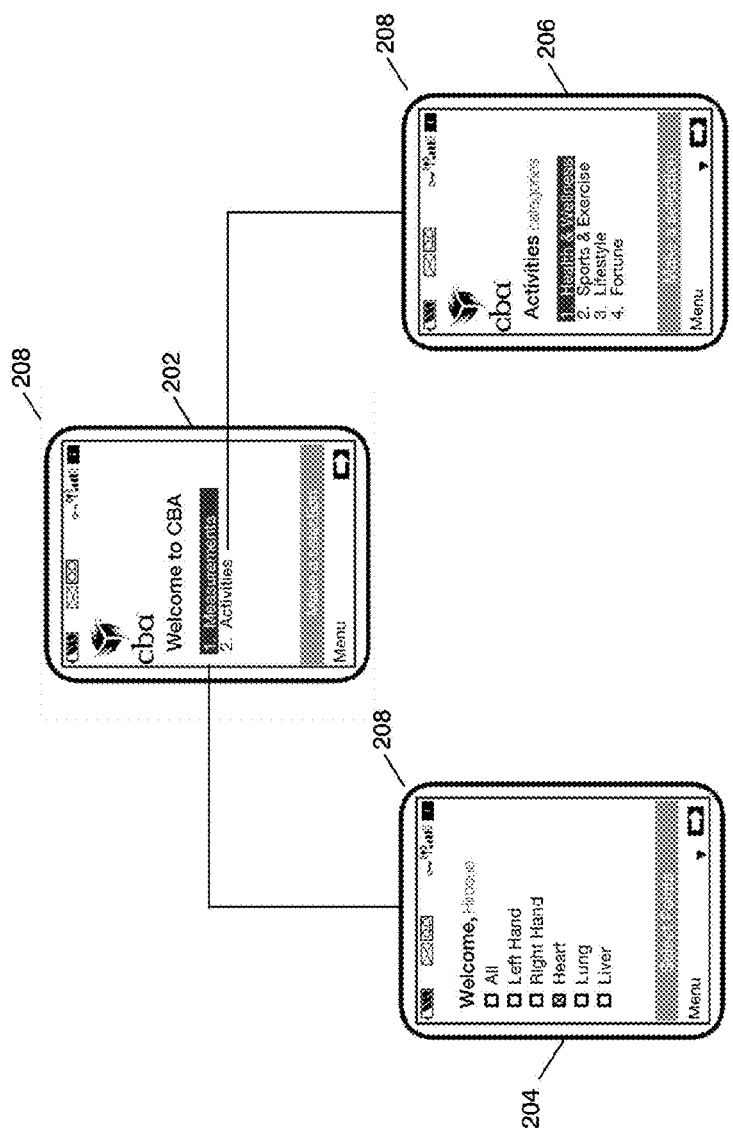

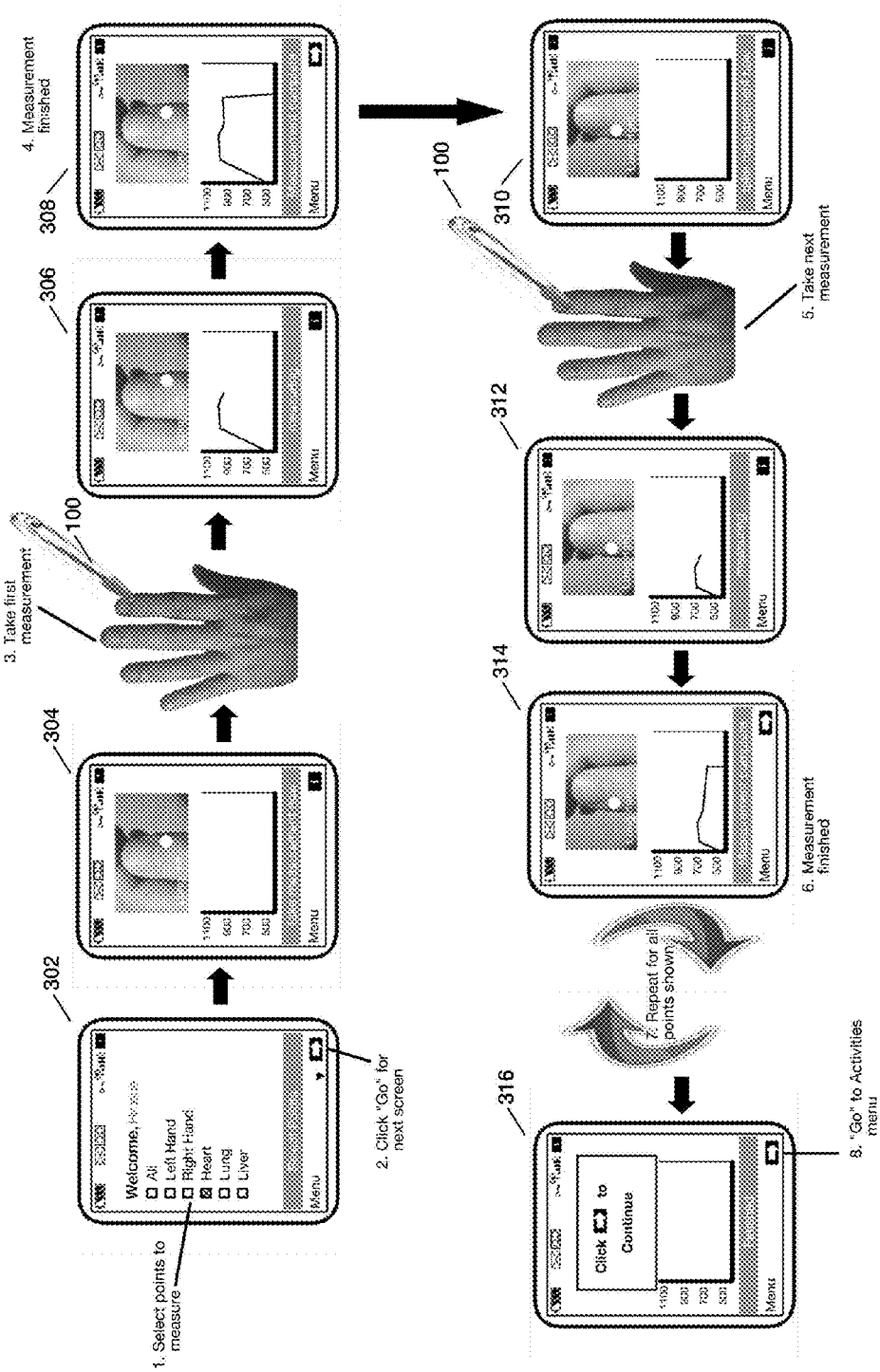
FIG. 3 Measurements

FIG. 4 Activities Menu

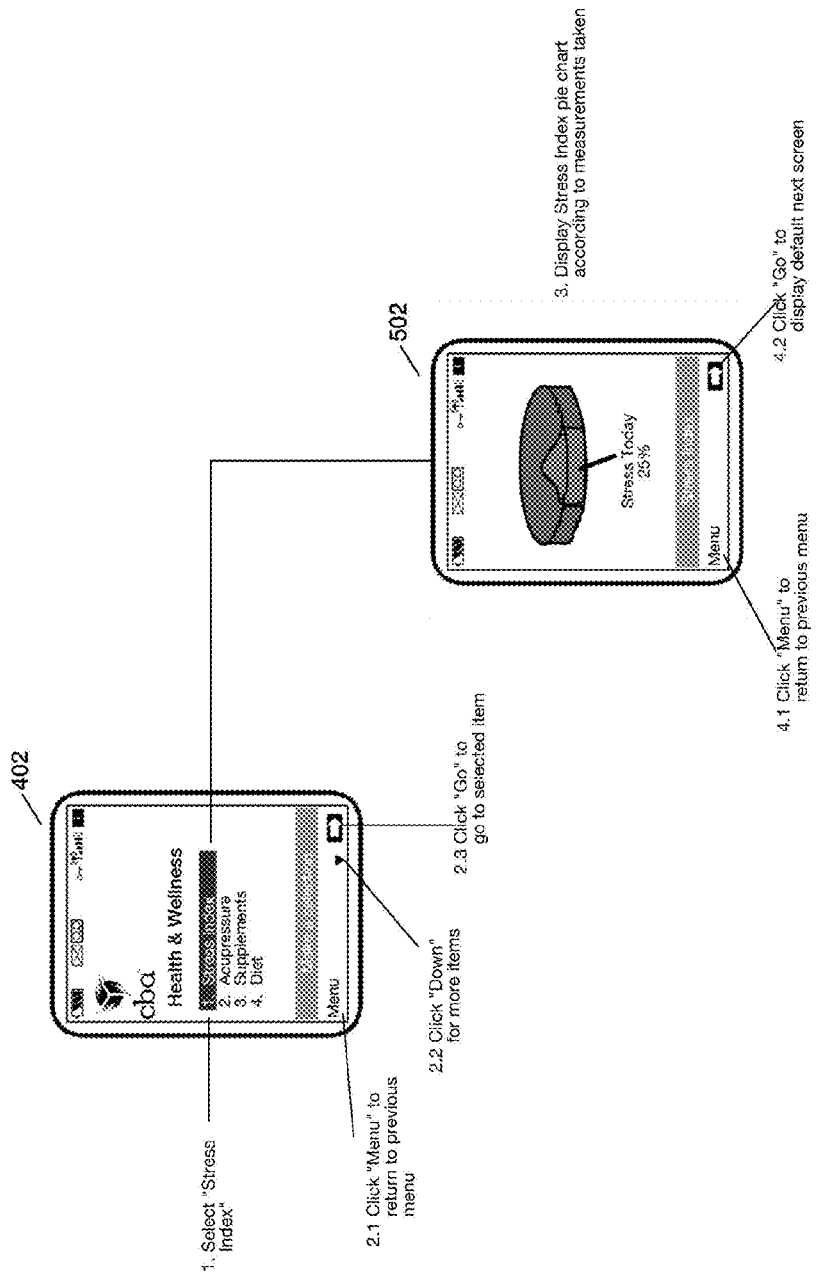

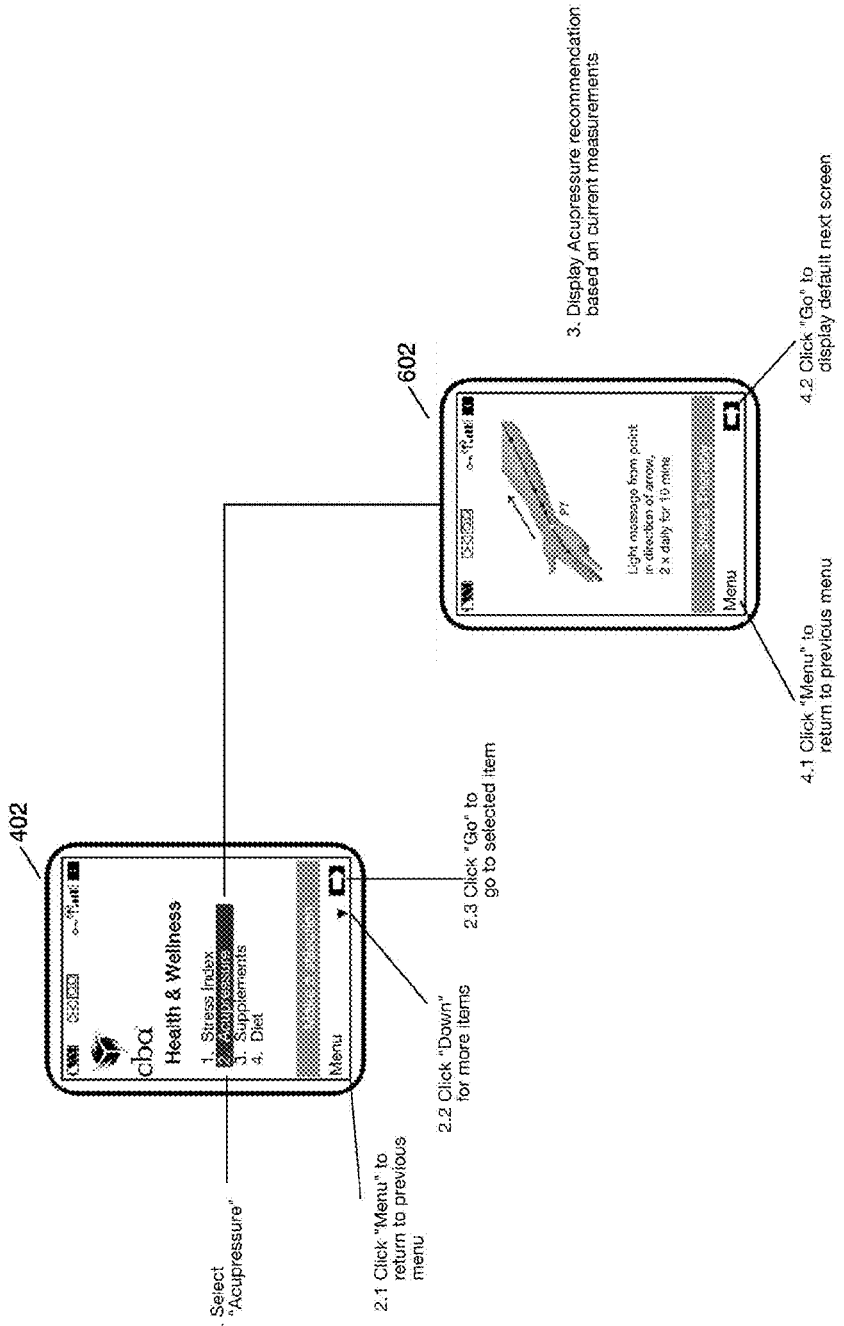

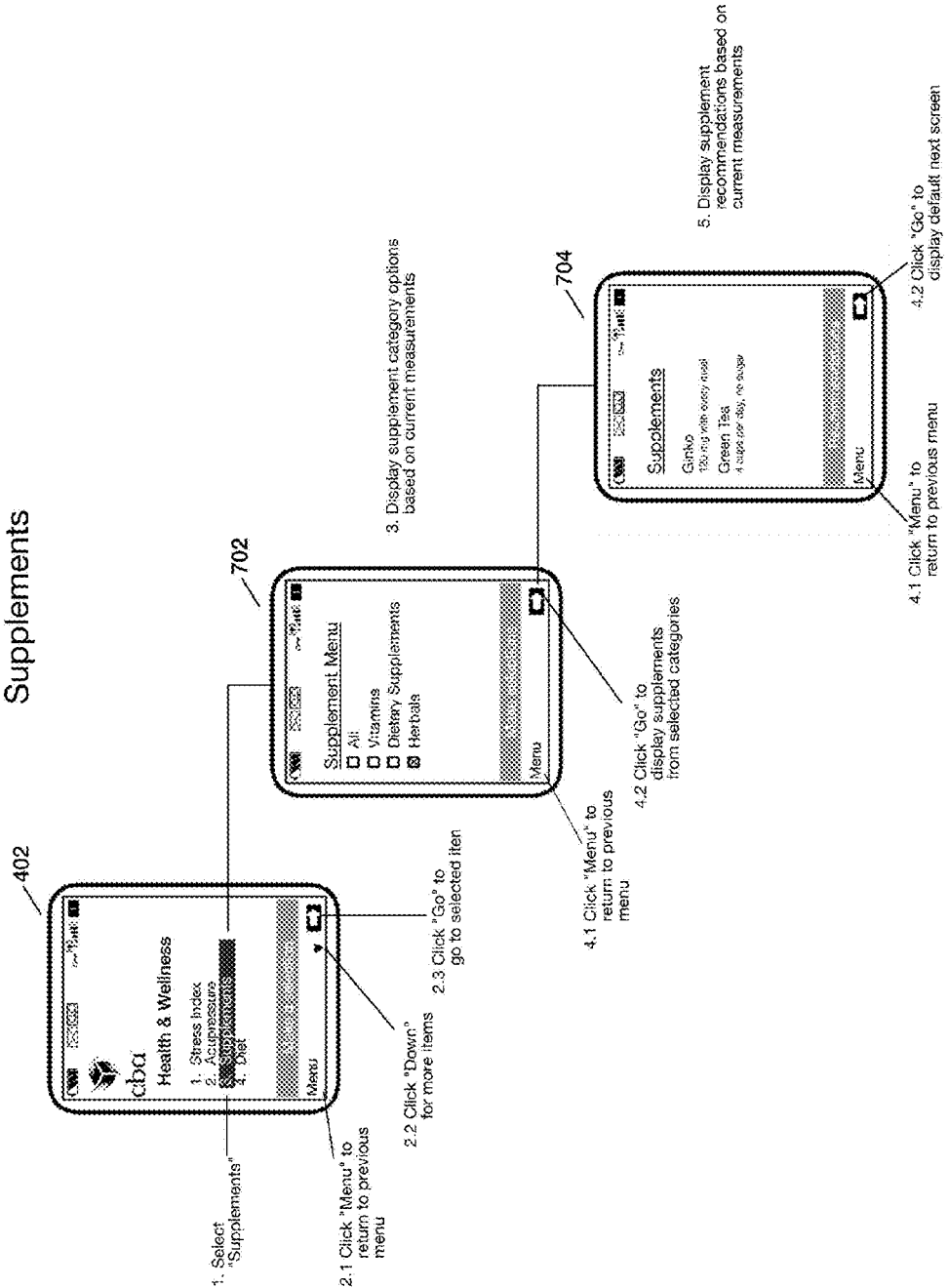

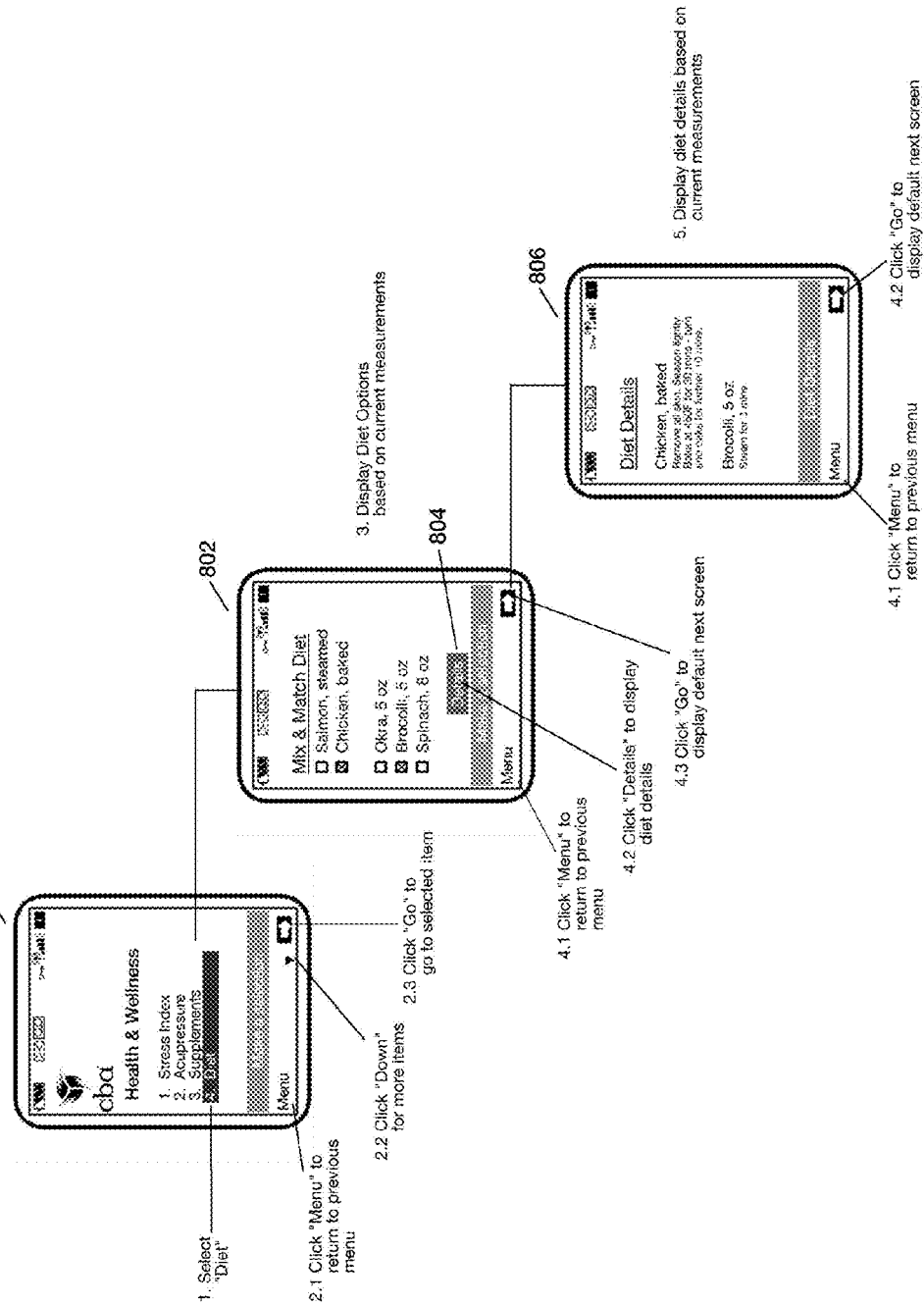

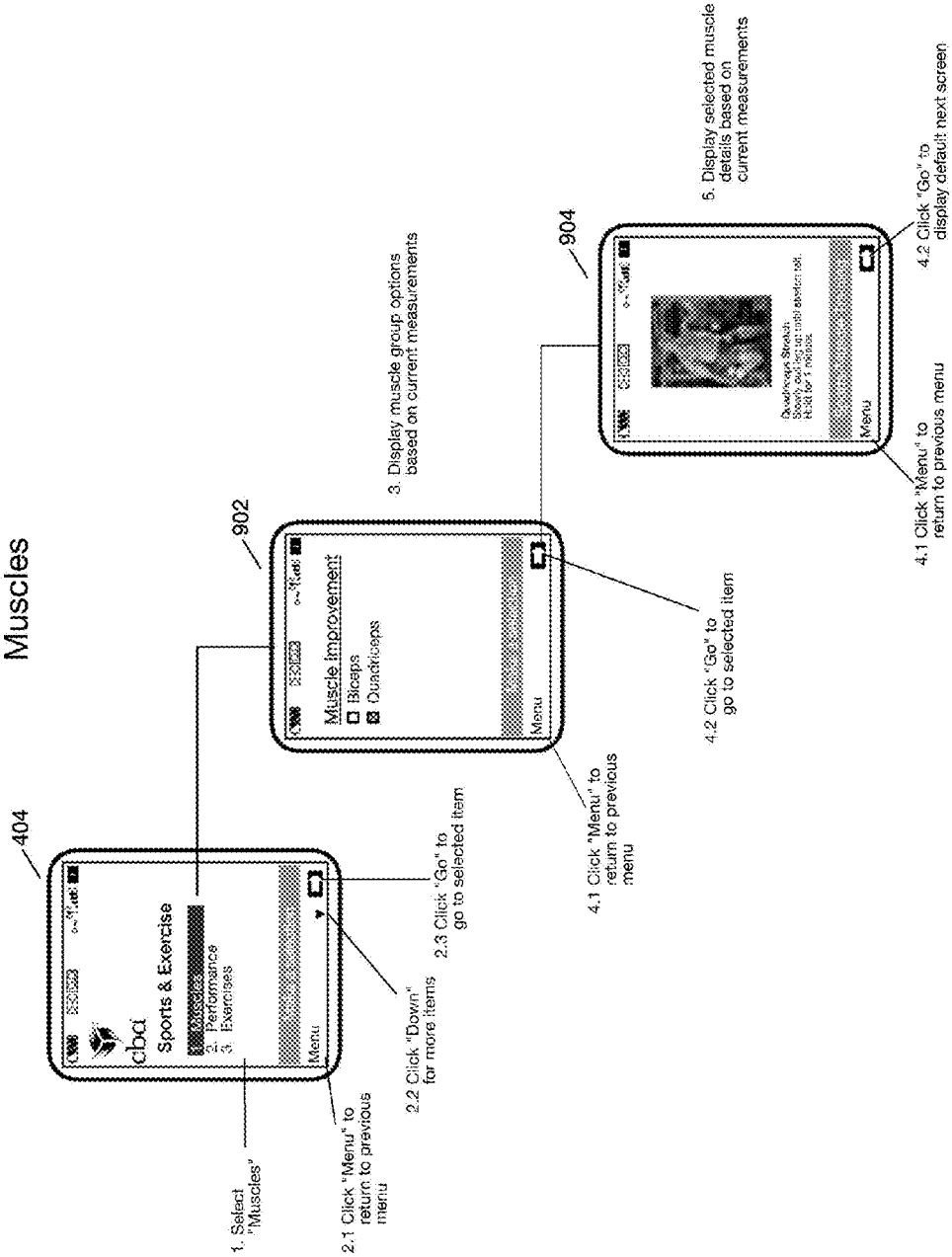

BIOFEEDBACK DEVICE DISPLAYING RESULTS ON A CELLULAR PHONE DISPLAY

CROSS REFERENCE TO RELATED APPLICATIONS

The present patent document claims the benefit of the filing date under 35 U.S.C. §119(e) of Provisional U.S. Patent Application Ser. No. 60/432,767, filed Dec. 12, 2002, which is hereby incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

REFERENCE TO COMPUTER PROGRAM LISTING APPENDIX

A computer program listing appendix is included containing computer program code listings on a CD-Rom pursuant to 37 C.F.R. 1.52(e) and is hereby incorporated by reference in its entirety. The total number of compact discs is 1 including 7 files and 1,486,848 bytes. The creation date of the compact disc is Apr. 15, 2004. The files included on the compact disc are listed below:

| Name of file | Size in bytes |
| --- | --- |
| CBA for i95c1-Specification.txt | 29K |
| DataManager.java | 17K |
| MassageManager.java | 5K |
| Measurement.java | 1K |
| MeasurementManager.java | 18K |
| ScanwebMidlet.java | 50K |
| VitalityManager.java | 21K |

BACKGROUND

The present invention relates generally to biofeedback devices. More particularly, the present invention relates to a biofeedback device displaying results on a cellular phone display.

A variety of devices have been developed for interaction with biofeedback devices. In general, a biofeedback device is any device which detects a body condition, such as an electrical or mechanical response, and produces a usable output. Interface devices are generally required in order to control the biofeedback device or present the output from the biofeedback device in a usable manner for the user.

For example, U.S. Pat. No. 6,386,882 B1 discloses remote delivery of software base training for implantable medical devices systems. A programmer establishes a radio frequency uplink from an implantable medical device to a remote, web based expert data center. The various wireless links to the device may be by satellite, Bluetooth, microwave or other disclosed technology. The programmer includes a display screen which displays telemetered out data or real time data. The programmer may also communicate data with a remote server.

Such prior devices have required elaborate communications capability and processing capability for processing data produced by the biofeedback device. In many applications, this level of complication, expense and investment by a user are not justified. For example, in some applications, a lightweight, hand-held biofeedback device is preferred or required. Similarly, custom communications circuits, using for example satellite frequencies, require an investment that is beyond the means of many potential users.

Therefore, there is a need in the art for a simplified, inexpensive biofeedback device which may be readily used by a large audience of users.

SUMMARY

A biofeedback device and system are disclosed. By way of introduction, the system, in one embodiment, includes a biofeedback device such as a device for measuring electrical parameters of the skin and a cellular telephone, possibly with additional equipment as well. In the system, the biofeedback device produces a biofeedback signal, which is an electrical signal indicative of biological activity or information. In the system, the biofeedback signal is displayed on a display screen on the cell phone.

The system has several possible embodiments. The currently envisioned embodiments all involve displaying the biofeedback signal on the cell phone display screen.

In a first embodiment, the hardware of the biofeedback device, consisting of a measuring electrode made of copper, a second electrode probably on the ball of the cell phone, circuitry, etc. are embedded in the cell phone itself. The hardware of the system operates in conjunction with software. The software also resides in the cell phone. A user operates the system to produce the biofeedback signal. After the measurements have been taken, the biofeedback signal is displayed on the screen.

In a second embodiment, the biofeedback device is contained as a standalone measuring pen that communicates with the cell phone, either through a wire or wirelessly. The software resides on the cellular telephone and produces a display on the display screen of the cellular phone.

In a third embodiment, the standalone measuring pen transmits data to a server. Subsequently, the data is conveyed to the cellular phone and displayed on the screen of the cell phone.

The foregoing introduction of the preferred embodiments has been provided only by way of introduction nothing in this section should be taken as a limitation of the following claims which define the scope of the invention.

BRIEF DESCRIPTION OF THE DRAWINGS

FIGS. 2-9 illustrate a menu system of the biofeedback system of FIG. 1.

DETAILED DESCRIPTION OF THE PRESENTLY PREFERRED EMBODIMENTS

Figure 1:
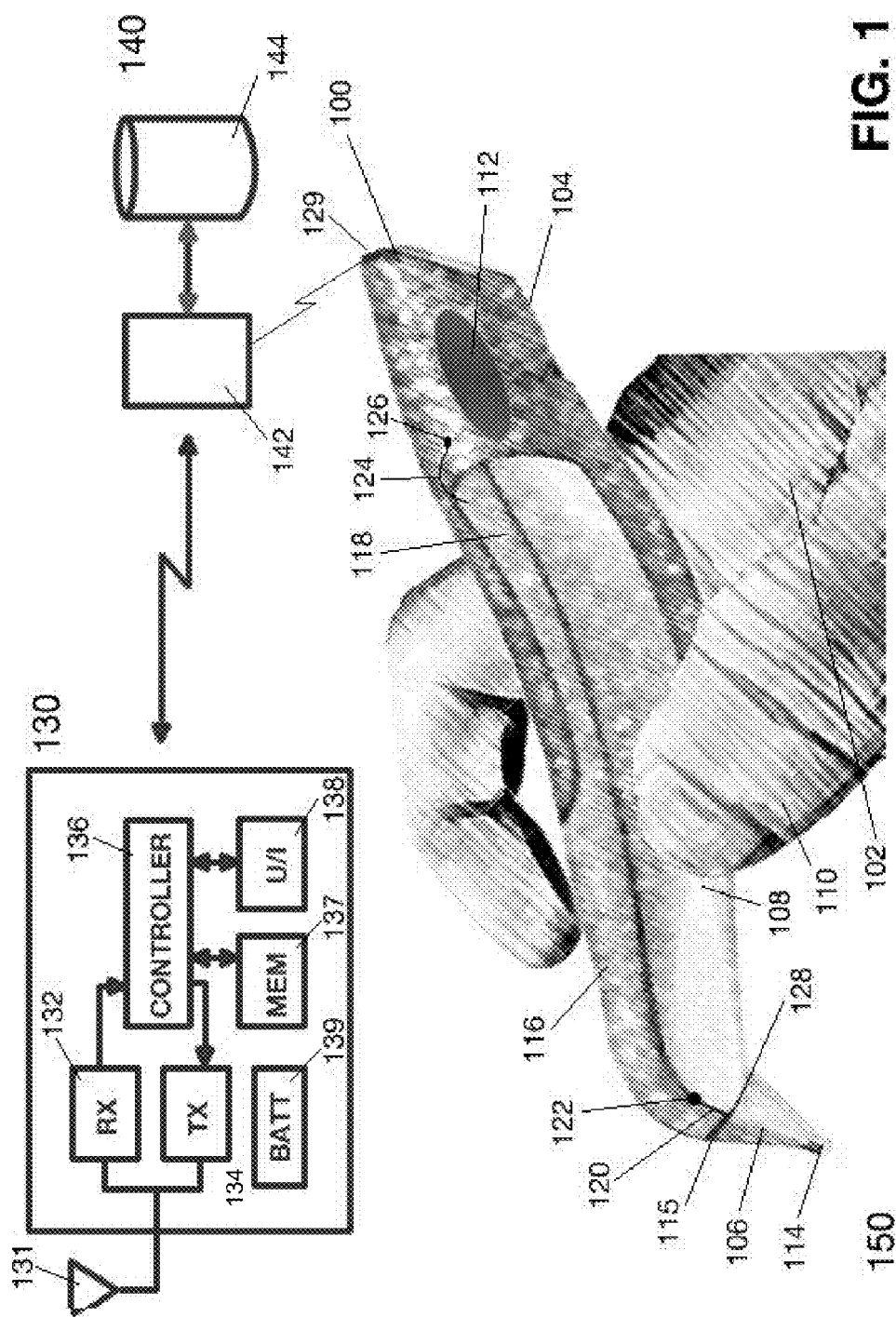
FIG. 1 is a block diagram of a biofeedback device and system.

FIG. 1 is a block diagram of a biofeedback device 100 and biofeedback system 150. The biofeedback system 150 includes biofeedback device 100, cellular telephone device 130 and server system 140. Some embodiments may omit some of the components of the biofeedback system 150 illustrated in FIG. 1, and some embodiments will include other components as well. The illustrated embodiment is intended to be exemplary only.

Biofeedback device 100 may be any device for detecting a body condition, such as an electrical or mechanical response, and produces a usable output. In the illustrated embodiment, the biofeedback device is configured as a device which measures an electrical property of human skin of the type disclosed in U.S. patent application Ser. No. 09/957,362, filed Sep. 20, 2001 in the name of Razvan Rentea and incorporated herein in its entirety by this reference.

The biofeedback device 100 includes a housing 104, a first electrode 106 and a second electrode 108. In the illustrated embodiment, the biofeedback device 100 is graspable by a human hand such as the human hand 102 so that the first electrode 106 may be placed in direct electrical contact with the skin of the human at a desired location and the second electrode 108 is in direct electrical contact with a digit or finger of the human hand 102 such as thumb 110. In other embodiments, the biofeedback device 100 may be located remotely from one or more of the electrodes 106, 108 but remain in electrical contact with the electrodes 106, 108.

In the illustrated embodiment, the biofeedback device 100 is an Electro Acupuncture According to Voll (EAV) device which measures electrical activity associated with acupuncture points. In particular, the biofeedback device 100 is configured to measure an electrical current at an acupuncture point and produce an indication. Accordingly, the biofeedback device 100 in a typical embodiment includes electrical circuitry contained within the housing 104, a battery also contained within the housing 104 and a user interface 112 for providing the indication and for otherwise providing user control of operation of the biofeedback device 100. The user interface 112 may include a digital display, a meter or any other suitable device for providing operating information including information about electrical activity of the skin measured by the biofeedback device 100. The electrical circuitry contained in the housing may be any suitable device or combination of devices for measuring electrical properties of the skin, such as Electro Acupuncture According to Voll. In particular, the electrical circuitry may include a processor operating under control of a computer readable program code for measuring one or more biofeedback signals of a user.

The electrodes 106, 108 are preferably electrically conductive, at least in part. Each electrode 106, 108 includes a skin-contacting portion configured for direct engagement with the skin of a patient. Thus, the first electrode 106 includes a skin-contacting portion in the form of a tapered tip 114 to contact an acupuncture point of a patient's skin. The second electrode 108 is disposed on a side 116 of the housing 104 and positioned so that the second electrode 108 presents a large, flat skin-contacting surface 118 which directly engages a finger of the patient's hand. In the illustrated embodiment, the thumb 110 of the hand 102 is engaged by the second electrode 108, but the second electrode 108 could alternatively be positioned or shaped in any suitable configuration to engage any other portion of the hand or other skin of the patient. The remainder of the electrode other than the skin-contacting portion may be formed of any suitable material, including even an insulator. For example, the shaft 115 of the first electrode 106 other than the tip 114 may be formed of a plastic material to provide advantages such as sterility, replaceability, mechanical support, and electrical isolation.

The conducting electrodes 106, 108 are also in electrical contact with electrical circuitry contained within the housing 104 for sensing an electrical signal at least one of the first electrode 106 and the second electrode 108. In the illustrated embodiment, a wire 120 extends from the first electrode 108 through an aperture 122 in the housing 104 to electrically contact the electrical circuitry in the housing 104. Similarly, a wire 124 extends from the second electrode 108 through an aperture 126 to electrically contact the electrical circuitry in the housing 104. Preferably, the wires 120, 124 are highly conductive to provide an accurate indication of an electrical parameter for measurement by the biofeedback device 100. Copper wire has been found to work well. In place, of the wires 120, 124, the electrical contact may alternatively be made directly to the electrical circuitry. For example, the probe formed by the first electrode 106 may be inserted into an end aperture 128 in the housing 104 so that a conductive end of the probe engages a conductive post, plate or annulus within the housing 104 which is in electrical contact with the electrical circuitry 104. Similarly, the second electrode 108 may engage a conductive post or plate under the electrode 108.

In accordance with one embodiment, at least one of the electrodes 106, 108 is an aluminum electrode. That is, at least one of the electrodes includes a skin-contacting portion which is made from or includes aluminum, an alloy or chemical compound of aluminum, either fully or in substantial part. In experiments with a device similar to the illustrated biofeedback device 100, it has been found that a first electrode made of copper or brass or other cuprous metal, in combination with a second or aluminum electrode made of aluminum foil, provides excellent results. Body own electrical currents in excess of 1600 nano-Amperes (nA) have been measured with this device. Other embodiments may be substituted and provide excellent results as well, as will be describe herein.

In one alternative embodiment, one of the electrodes 106, 108 is an aluminum electrode and the other electrode includes silver chloride. In this manner, the aluminum electrode may be used in combination with a silver chloride electrode, which is widely available. In another alternative embodiment, the other electrode is also aluminum or a conductor made with a substantial portion of aluminum. Other equivalent metals, alloys or combinations of materials may be substituted as well. The relative positioning and location of the aluminum electrode and the first electrode may be varied also. For example, in the illustrated embodiment, the first electrode 106 may be formed of aluminum material and the second electrode 108 may be formed of another conductor such as a cuprous metal like brass, silver chloride or even aluminum. By cuprous metal, it is meant a metal or alloy or other conductive material containing copper in substantial portion.

It has been found that the configuration and dimensions of the aluminum electrode can have a strong effect on performance of the biofeedback device. In one embodiment, the aluminum electrode is formed of a metallic layer having a predetermined thickness. Preferably, the thickness of the metallic layer is less than about 0.25 millimeters (mm). It has been found that when aluminum is used, thicker metallic layers do not work well or at all. Most preferably, the thickness of the metallic layer is about 0.1 mm.

In one embodiment, the metallic layer is an aluminum film. The film may be formed using aluminum foil adhered to a substrate. Alternatively, the film may be formed by depositing an aluminum film on a substrate, for example using a chemical vapor deposition or sputtering process. The substrate preferably provides mechanical support and protection for the aluminum foil or film. In a simple and inexpensive embodiment, a piece of aluminum foil having a suitable thickness is taped directly to the skin of the patient or, as shown in the illustrated embodiment, to the housing of the biofeedback device 100.

It is a particular advantage of the electrodes described herein that they are configured for direct contact with the skin of a patient. No conductive paste or gel is needed. In the illustrated embodiment, the skin of the thumb 110 is contacted when the device 100 is grasped by the patient. The tip 114 is configured for directly contacting the skin at a remote location of the patient. More particularly, the first electrode is pointed at the tip 114 to contact an acupuncture point of the patient's skin. The patient may grasp the device 100 as shown and place the tip 114 against selected acupuncture points of the patient's body. This embodiment is thus well adapted for measuring Electro Acupuncture according to Voll associated with acupuncture points of the patient's skin.

It is believed that the aluminum electrode has a higher contact resistance with the skin than electrodes of other materials, such as cuprous metals or silver chloride. This higher contact resistance suggests that an aluminum electrode would be a poor choice for measuring electrical properties of the skin, since the higher contact resistance could interfere with reliable and accurate measurements of small electrical currents and potentials. However, after much experimentation with different materials and mechanical properties, the opposite has been found to be true. The use of an aluminum electrode is an important feature of the embodiments disclosed herein.

In another embodiment, the first electrode 106 and the second electrode 108 may be combined as an electrode set. In this embodiment, an electrode set 130 for a biofeedback device such as the biofeedback device 100 includes a first metallic electrode such as first electrode 106 formed for electrical contact with a measuring portion such as the internal electrical circuitry of the biofeedback device and an aluminum electrode such as second electrode 108 formed for electrical contact with the measuring portion of the biofeedback device. The respective electrodes should have the electrical and mechanical properties as described herein. The electrode set 130 may in this manner be provided as replacement electrodes for use with the biofeedback device if the original electrodes become damaged, worn, dirty or otherwise need replacement.

In a further embodiment, the shaft 115 of the first electrode 106 may be keyed to match the end aperture 128 in the housing 104 so that only approved electrode sets may be used with the biofeedback device. That is, the end of the shaft which is inserted in the end aperture 128 in the housing 104 may have a particular outer shape which mechanically engages the end aperture 128 which a matching particular inner shape. Alternatively, one or both electrodes 106, 108 may provide a predetermined electrical response which is required for operation of the biofeedback device. These features may provide advantages such as ensuring that only high-quality conforming electrodes are used with the biofeedback device.

The biofeedback device 100 further includes circuitry 129 for external data communication. In some embodiments, the circuit 129 includes a network interface for wire line connection with the server system 140. Data may be communicated between the server system 140 and the network interface. The network interface may be a modem for analog communication such over a telephone link, or may be a digital modem or transceiver circuit for digital data communication. Alternatively, the network interface may be a wireless circuit of any suitable type for wireless communication with the server system 140.

The circuitry 129 for external data communication further includes a wireless interface for wireless communication with the cellular telephone device 130. The wireless interface communicates according to a wireless protocol. Examples include Bluetooth, IEEE Standard 802.11 and related standards, and cellular and Personal Communication System (PCS) transceiver circuits. Also, circuits which communicate using unlicensed frequency bands may be used for data communication with the cellular telephone device 130. Alternatively, a wire and suitable connectors may be used for connecting the biofeedback device 100 with the cellular telephone device 130.

The cellular telephone device 130 may be any electronic device which includes cellular, PCS or cellular-type communication capability. Generally, cellular service is provided to the cellular telephone device 130 on a subscription basis. The cellular telephone device 130 is configured for radio communication with remote base stations of a cellular, PCS or trunked radio system. Through the wireless link to the base station, the cellular telephone device 130 may communicate with the public switched telephone network (PSTN).

The cellular telephone device 130 may also be referred to as a mobile, portable, handheld, user equipment (UE), cell phone or radiotelephone. The cellular telephone device 130 in the illustrated embodiment includes an antenna 131, a receiver 132, a transmitter 134, a controller 136, memory 137, user interface 138 and battery 139.

The antenna 131 transforms electromagnetic energy to electrical signals provided to the receiver 132, and transforms electrical signals from the transmitter 134 to electromagnetic energy for transmission to remote radio receivers. The receiver 132 responds to the electrical signals from the antenna 131 to produce detected data for the controller 136. The receiver 132 may include circuits such as filters and demodulators. The transmitter 134 responds to formatted data from the controller to provide the electrical signals to drive the antenna 131. The transmitter 134 may include circuits such as modulators and filter. The antenna 131, the receiver 132 and the transmitter 134 together form a radio communication circuit for two-way radio communication with remote radio devices such as a base station.

The controller 136 controls operation of the cellular telephone device 130. The controller 136 may be implemented as a processor, microprocessor, digital signal processor (DSP) or any other logic circuit or combination of circuits providing control functions. The controller 136 operates in response to data and program instructions stored in the memory 137. In one mode, the controller 136 controls the radio communication circuit by directing the tuning, activation and deactivation of the circuit.

The user interface 138 provides user control of the cellular telephone device 130. In typical embodiments, the user interface 138 includes a keypad, a display screen, a microphone and a speaker. In the particular exemplary embodiment described herein the user interface 138 includes a display sufficiently large to display graphical data, text and photographs. The user interface 138 accordingly includes one or more software application programs for controlling the biofeedback measuring device in measuring biofeedback signals, processing received data and producing a display based on the data. The software application programs may be configured as computer readable program code and stored in the memory 137. The battery 139 provides operating power for the cellular telephone device 130.

The cellular telephone device 130 may be embodied as a conventional cellular or PCS telephone, or as a personal digital assistant (PDA) having radio communication capability. In other embodiments, the cellular telephone device 130 may be combined with other equipment such as a portable or laptop computer. In another embodiment, the cellular telephone device 130 combined with the biofeedback device 100 in a housing appearing the same as a conventional cell phone.

In some embodiments, in addition to the cellular-type communication ability provided by the radio communication circuit, the cellular telephone device 130 also includes a transceiver circuit for two-way wireless data communication. The transceiver circuit implements a wireless data protocol such as Bluetooth or IEEE standard 802.11 or related standards. In the biofeedback system 150, the transceiver circuit communicates data with the circuitry 129 for external data communication of the biofeedback device 100. Data and other information received from the circuitry 129 for external data communication is processed by software applications of the cellular telephone device 130 including the user interface 138 and a suitable display is provided on the display screen of the user interface 138. In some embodiments, the cellular telephone device 130 communicates wirelessly with the server system 140.

The server system 140 includes a server computer 142 and a database 144. The server computer 142 may be any suitable processing device for serving applications and data with the biofeedback device 100 and the cellular telephone device 130. The server computer 142 may interact with other computers or other equipment, located with the server or accessible over a communication link, to provide further processing of data. The database 144 stores data for use by the server computer 142.

In a first embodiment of the biofeedback system 100, the biofeedback device 100 and the cellular telephone device 130 are combined in a single unit. That is, the circuitry and electrodes of the biofeedback device are embedded in the cell phone itself. The electrodes are located on the outside surface of the cell phone housing for access by a user. The hardware of the system operates in conjunction with software. The software also resides in the cell phone. A user operates the system to measure biofeedback from the human body and produce a biofeedback signal. After the measurements have been taken, measurements or other information about the biofeedback signal is displayed on the screen. Additional data and information derived from the biofeedback signal or based on the biofeedback signal and measurements may also be presented on the display screen. The user interface may be manipulated to access the additional information as will be described in greater detail hereinbelow.

In a second embodiment, the biofeedback device is contained as a standalone measuring pen that communicates with the cell phone 130, either through a wire or wirelessly, similar to the embodiment illustrated in FIG. 1. Software resides on the biofeedback device to take actual biofeedback measurements such as electrical activity of the skin. Software also resides on the cellular telephone and produces a display on the display screen of the cellular phone 130. Information about the measurements taken by the biofeedback device 100 is communicated to the cell phone 130 and used to produce the display. The software resident on the cell phone 130 may produce additional information accessible through the user interface 138.

In a third embodiment, the standalone measuring pen takes biofeedback measurements and transmits data and information about the measurements to a server such as the server system 140. The data may be communicated wirelessly or by wire line connection. Subsequently, the data is conveyed to the cellular phone 130 and displayed on the screen of the user interface 138 of the cell phone 130.

Other embodiments may be arranged as well. In general, the display screen of the cellular telephone device 130 is used to provide biofeedback information including a menu system for additional information based on measured biofeedback data.

FIGS. 2-10 illustrate one embodiment of a menu system for use in the cellular telephone device 130 of the biofeedback system 100 of FIG. 1. It is to be noted that the illustrated menu system is exemplary only. Other menu systems may be readily developed and provide additional capabilities.

FIG. 2 is a series of screen shots illustrating a portion of the menu system of the biofeedback system of FIG. 1. FIG. 2 illustrates a Welcome Menu 202. In the Welcome Menu 202, the user is given two menu options and invited to "make a selection". Within the Welcome Menu, the first option is illustrated as a screen shot 204, which shows possible measurement activity for the biofeedback system. Possible activities include taking measurements for all possible body parts, the left hand, the right hand, the heart, the lung, and the liver. The user is invited to select the points to be measured.

From the Welcome Menu of the screen shot 202, a second option is the activities menu showed in screen shot 206. The activities illustrated for selection in this embodiment include Health & Wellness, Sports & Exercise, Lifestyle and Fortune.

In each of the menu screens, other user information icons 208 of the cell phone display continue to be displayed along with the current menu. These icons include, for example, a voice mail indicator, a text message indicator, and a signal strength indicator. These icons continue to be displayed throughout operation of the system so that the user may continue to monitor cell phone operation.

FIG. 3 illustrates screen shots available following access to the Measurements menu of screen shot 204, FIG. 2. FIG. 2 also illustrates operation of the device for monitoring biofeedback information.

Screen shot 302 in FIG. 3 illustrates operation of the biofeedback device to select one or more biofeedback points to measure. The user operates the user interface of the cellular phone to select the desired input value of the menu. For example, the user interface may include a touch sensitive screen for receiving user input or a series of software programmable keys for data entry. Further, the user operates the Go icon shown in the lower right corner of the display to advance to the next menu screen, as shown in screen shot 304. Screen shot 304 illustrates a photograph of the desired biofeedback point on the human body and a graphical display of biofeedback information. Further, screen shot 304 provides user direction, specifically "take measurement now." As illustrated in FIG. 3, the user applies the biofeedback device 100 to the designated biofeedback point on the user body, taking a first measurement. Screen shot 306 illustrates operation in progress, providing the user feedback for measuring the biofeedback sign and producing on the display a graphical image of measured biofeedback data. Thus, the data is measured by the biofeedback device and communicated to the cell phone for display and further processing.

Screen shot 308 illustrates the next step in the process, where the measurement is complete. In the screen shot 308, the photograph of the user body part and a designation of the biofeedback point continue to be displayed and the complete graph of biofeedback data is produced.

At screen shot 310, the user is invited to move the biofeedback device 100 to the next appropriate biofeedback point and instructed to "take measurement now." As illustrated in FIG. 3, the biofeedback device is advanced to the next indicated biofeedback point. At screen shot 312, user feedback is provided to indicate that the biofeedback device is currently measuring the biofeedback information. A data graph is provided to illustrate the process. When the process is complete, screen shot 314 illustrates that the biofeedback data has been collected and the measurement is complete. The process illustrated in screen shots 304, 306, 308, 310, 312, 314 is repeated for all points shown. The control software steps through the predefined points, provides a guiding illustration and provides user feedback as to the progress of the measurement. When the process for all points is completed, screen shot 316 illustrates that the process is finished and invites the user to click the Go icon to advance to the next step.

FIG. 4 illustrates the screen shot 206 containing the activities menu of FIG. 2. FIG. 4 illustrates sub-menus available within the activities menu in the illustrated embodiment. Screen shot 402 illustrates a sub-menu under the Health & Wellness selection of the activities menu. The screen shot 402 shows that the Health & Wellness menu includes topics of Stress Index, Acupressure, Supplements and diet. The user then manipulates the user interface of the cellular phone to access any of these sub-menu items.

Screen shot 404 illustrates that the Sports & Exercise selection of the activities menu shown in screen shot 206 includes sub-menu items "Muscles" "Performance" and "Exercises." Again, the user can manipulate the user interface to access any of these items from this menu shown in screen shot 404.

Screen shot 406 illustrates the options available in a sub-menu after selecting the menu item Lifestyle on the Activities Menu illustrated in screen shot 206. The Lifestyle sub-menu items include Biofun, Looking Good and Personal Lifestyle. Screen shot 408, in turn, illustrates the menu items available in the Biofun sub-menu after selection using the menu illustrated in screen shot 406. The Biofun menu items include BioMatching, Feel Good Color and Feel Good Music. Screen shot 410 illustrates the sub-menu items available upon selection of the Looking Good menu item illustrated in screen shot 406 showing the lifestyle categories sub-menu. The Looking Good sub-menu selection options include Cosmetics and Fashion. Screen shot 412 illustrates sub-menu items available upon selection of the Personal Lifestyle menu item illustrated in the Lifestyle menu of screen shot 406. The Personal Lifestyle sub-menu includes only a single entry in this embodiment, Sexual Performance.

Screen shot 414 illustrates a sub-menu available upon selection of the Fortune menu item illustrated in the screen shot 206 showing the activities menu. Within the Fortune menu, two options include I Ching Oracle and Lucky Direction. Again, by manipulation of the user interface of the cellular phone, the user may access any of these menu and sub-menu items.

FIG. 5 illustrates operations available upon actuation of the Health & Wellness menu illustrated in screen shot 402, FIG. 4. In particular, FIG. 5 illustrates the operation of the Stress Index menu item. Upon selecting the Stress Index item on the Health & Wellness menu, and upon clicking the go icon to go to the selected menu item, a display illustrated in the screen shot 502 is produced on the cell phone display. In this embodiment, the display shows a Stress Index pie chart according to the measurements taken, for example in the measurement process illustrated in FIG. 3. Additional menu items are provided as shown in the screen shot 502.

As further illustrated in the screen shot 402, the Health & Wellness menu includes additional options. By clicking on the menu icon at the lower left corner of the display shown in the screen shot 402, the user may navigate back to the previous menu in the menu system. By clicking on the down arrow in the lower right corner, the user may display more items in the Health & Wellness sub-menu.

FIG. 6 illustrates screen shots of the menu system displayed on the cellular phone of the biofeedback system of FIG. 1 for measuring acupressure of the patient. The screen shot 402 shows selection of the Acupressure menu item. Upon activation of the Go icon in the lower right corner of the display, the display is changed to screen shot 602. Screen shot 602 illustrates an acupressure recommendation based on the current measurements taken, for example during the process such as that illustrated in FIG. 3.

FIG. 7 illustrates information available upon selection of the Supplements menu item illustrated in the screen shot 402 showing the Health & Wellness menu. In screen shot 402, upon selecting the Supplements menu and clicking the Go icon, the display of the cell phone is changed to show the display shown in the screen shot 702, which provides a Supplements menu. In this embodiment, the Supplements menu includes checkable items "All," "Vitamins," "Dietary Supplements" and "Herbals." In the illustrated example, the Herbals entry has been selected and, upon clicking the Go icon in the lower right corner of the display illustrated in screen shot 702, screen shot 704 is displayed. In this example, the display shows supplement recommendations based on current measurements taken during a measurement process. In this example, herbal supplements of Ginkgo and Green Tea are recommended for the user.

FIG. 8 illustrates the operation of the biofeedback system upon selection of the Diet menu item within the Health & Wellness menu illustrated in screen shot 402. Upon selection of the Diet menu item and clicking of the Go icon in the display shown in screen shot 402 of FIG. 8, the display illustrated in screen shot 802 is produced on the display of the cellular phone. A screen shot 802 displays diet options for the user based on current measurements taken during a measurement process. In the illustrated example, diet options include steamed salmon, baked chicken and the specified amounts of okra, broccoli and spinach. A Details menu item 804 is also available and may be selected by the user for displaying additional diet details. The additional diet details are illustrated in the display shown in the screen shot 806. In this example preparation suggestions are provided for the checked diet items shown in the screen shot 802. Additional details may be available.

FIG. 9 illustrates sub-menu items available within the muscles item of the Sports & Exercise menu illustrated in screen shot 404. Upon selection of the menu item Muscles, screen shot 902 is displayed. The display illustrated in screen shot 902 displays muscle group options based on current measurements which should be improved. In the illustrated example, these include biceps and quadriceps. The user is further invited in the display of screen shot 902 to make a selection among the illustrated items. Upon selecting quadriceps, the display of screen shot 904 is produced on the display of the cell phone. This display shows selected muscle details based on current measurements. In the illustrated, exemplary embodiment, a photograph of a model is provided along with directions for stretching or exercising the identified muscles.

From the foregoing, it can be seen that the presently disclosed embodiments provide an improved biofeedback device and system. One or more biofeedback signals are measured by the biofeedback device, processed, and a display based on the measurements is produced on a cellular telephone device. A menu system allows easy access to the measured data, interpretation of the data and recommendations based on the measured data. The recommendations are keyed to personal activities of the user, such as diet, exercise and health care so that a complete health promoting regimen is provided by the biofeedback device.

While a particular embodiment of the present invention has been shown and described, modifications may be made. It is therefore intended in the appended claims to cover such changes and modifications which follow in the true spirit and scope of the invention.

The invention claimed is:

1. A biofeedback system comprising:
 a cellular telephone device, including
  a data processor, and
  a user interface including a display screen;
 a biofeedback measuring device configured to contact the skin of a user and detect and measure a body own electrical current occurring at an acupuncture point on the user's body and to produce one or more biofeedback signals derived from the electrical current;
 first computer readable program code stored in a computer readable medium for controlling the biofeedback measuring device in producing the one or more biofeedback signals;
 second computer readable program code stored in a computer readable medium for producing a display on the display screen based on the one or more biofeedback signals; and
 third computer readable code stored in a computer readable medium for producing a user assistance display on the display screen identifying the acupuncture point on the user's body for measuring the body own electrical current.

2. The biofeedback system of claim 1 wherein the biofeedback measuring device is operable to communicate with the cellular telephone device.

3. The biofeedback system of claim 1 wherein the biofeedback measuring device is embedded within the cellular telephone device.

4. The biofeedback system of claim 1 wherein the third computer code produces the user assistance display user feedback for measuring the biofeedback signal and producing on the display a graphical image of measured biofeedback data.

* * * * *